United States Patent
Dryga et al.

(10) Patent No.: US 10,416,155 B2
(45) Date of Patent: *Sep. 17, 2019

(54) METHODS FOR ISOLATING A TARGET ANALYTE FROM A HETEROGENOUS SAMPLE

(71) Applicant: DNAE Group Holdings Limited, London (GB)

(72) Inventors: Sergey A. Dryga, Albuquerque, NM (US); Victor C. Esch, Albuquerque, NM (US); Lisa-Jo Ann Clarizia, Albuquerque, NM (US); Eddie W. Adams, Albuquerque, NM (US); Thearith H. Ung, Albuquerque, NM (US); Ravil A. Sitdikov, Albuquerque, NM (US)

(73) Assignee: DNAE Group Holdings Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/969,493

(22) Filed: May 2, 2018

(65) Prior Publication Data

US 2018/0252709 A1    Sep. 6, 2018

Related U.S. Application Data

(60) Continuation of application No. 15/332,679, filed on Oct. 24, 2016, now Pat. No. 9,970,931, which is a division of application No. 13/952,130, filed on Jul. 26, 2013, now Pat. No. 9,476,812, which is a continuation-in-part of application No. 13/091,510, filed on Apr. 21, 2011, now Pat. No. 8,841,104.

(60) Provisional application No. 61/739,616, filed on Dec. 19, 2012, provisional application No. 61/326,588, filed on Apr. 21, 2010.

(51) Int. Cl.
| | |
|---|---|
| *C12Q 1/00* | (2006.01) |
| *G01N 33/543* | (2006.01) |
| *G01N 1/34* | (2006.01) |
| *C07K 16/12* | (2006.01) |
| *C12N 13/00* | (2006.01) |
| *G01N 33/569* | (2006.01) |
| *C12Q 1/24* | (2006.01) |

(52) U.S. Cl.
CPC ... *G01N 33/54333* (2013.01); *C07K 16/1203* (2013.01); *C07K 16/1267* (2013.01); *C12N 13/00* (2013.01); *C12Q 1/24* (2013.01); *G01N 1/34* (2013.01); *G01N 33/569* (2013.01); *C07K 2317/33* (2013.01)

(58) Field of Classification Search
CPC .................................................. G01N 33/54333
See application file for complete search history.

(56) References Cited

U.S. PATENT DOCUMENTS

| | | | | |
|---|---|---|---|---|
| 8,841,104 B2 * | 9/2014 | Dryga | ...................... | C07K 1/22 435/173.9 |
| 9,696,302 B2 * | 7/2017 | Dryga | ...................... | C07K 1/22 |
| 9,970,931 B2 * | 5/2018 | Dryga | ................ | C07K 16/1267 |
| 2004/0087032 A1 * | 5/2004 | Chandler | ............. | C12Q 1/6816 436/164 |

* cited by examiner

*Primary Examiner* — Albert M Navarro
(74) *Attorney, Agent, or Firm* — Brown Rudnick LLP; Thomas C. Meyers

(57) ABSTRACT

The invention generally relates to methods of using compositions that include sets of magnetic particles, members of each set being conjugated to an antibody specific for a pathogen, and magnets to isolate a pathogen from a body fluid sample.

10 Claims, No Drawings

METHODS FOR ISOLATING A TARGET ANALYTE FROM A HETEROGENOUS SAMPLE

RELATED APPLICATIONS

The present application is a continuation of U.S. nonprovisional patent application Ser. No. 15/332,679, filed Oct. 24, 2016, and set to issue as U.S. Pat. No. 9,970,931 which is a divisional of U.S. nonprovisional patent application Ser. No. 13/952,130, filed on Jul. 26, 2013 and set to issue as U.S. Pat. No. 9,476,812, which is a continuation-in-part of U.S. nonprovisional patent application Ser. No. 13/091,510, filed Apr. 21, 2011, now U.S. Pat. No. 8,841,104, which claims priority to and the benefit of U.S. provisional patent application Ser. No. 61/326,588 filed Apr. 21, 2010. In addition, the '130 application claims the benefit of and priority to U.S. provisional patent application Ser. No. 61/739,616, filed Dec. 19, 2012. The content of each application is incorporated by reference herein in its entirety.

FIELD OF THE INVENTION

The invention generally relates to methods of using compositions that include sets of magnetic particles and magnets to isolate a pathogen from a body fluid sample.

BACKGROUND

Blood-borne pathogens are a significant healthcare problem. A delayed or improper diagnosis of a bacterial or fungal infection can result in sepsis, a serious, and often deadly, inflammatory response to the infection. Sepsis is the $10^{th}$ leading cause of death in the United States. Early detection of bacterial infections in blood is the key to preventing the onset of sepsis. Traditional methods of detection and identification of blood-borne infection include blood culture and antibiotic susceptibility assays. Those methods typically require culturing cells, which can be expensive and can take as long as 72 hours. Often, septic shock will occur before cell culture results can be obtained.

Alternative methods for detection of pathogens, particularly bacteria and fungi, have been described by others. Those methods include molecular detection methods, antigen detection methods, and metabolite detection methods. Molecular detection methods, whether involving hybrid capture or polymerase chain reaction (PCR), require high concentrations of purified DNA for detection. Both antigen detection and metabolite detection methods also require a relatively large amount of pathogens and have high limit of detection (usually>$10^4$ CFU/mL), thus requiring an enrichment step prior to detection. This incubation/enrichment period is intended to allow for the growth of bacteria or fungi and an increase in cell numbers to more readily aid in identification. In many cases, a series of two or three separate incubations is needed to isolate the target bacteria or fungus. However, such enrichment steps require a significant amount of time (e.g., at least a few days to a week) and can potentially compromise test sensitivity by killing some of the cells sought to be measured.

There is a need for methods for isolating target analytes, such as bacteria, from a sample, such as a blood sample, without an additional enrichment step. There is also a need for methods of isolating target analytes that are fast and sensitive in order to provide data for patient treatment decisions in a clinically relevant time frame.

SUMMARY

The present invention provides methods for isolating pathogens in a biological sample. The invention allows the rapid detection of pathogen at very low levels in the sample; thus enabling early and accurate detection and identification of the pathogen. The invention is carried out using sets of magnetic particles, members of each set being conjugated to a binding element, such as an antibody, that is specific for a pathogen. The invention allows detection of pathogen in a heterogeneous biological sample at levels, for example, from about 10 CFU/ml to about 1 CFU/ml or lower.

Methods of the invention involve introducing magnetic particles to a biological sample (e.g., a tissue or body fluid sample). The sample is incubated to allow the particles to bind to pathogen in the sample, and a magnetic field is applied to capture pathogen/magnetic particle complexes on a surface. Optionally, the surface can be washed with a wash solution that reduces particle aggregation, thereby isolating pathogen/magnetic particle complexes. A particular advantage of compositions of the invention is for capture and isolation of bacteria and fungi directly from blood samples at low concentrations that are present in many clinical samples (as low as 1 CFU/ml of bacteria or fungi in a body fluid). Preferably, the magnetic particles comprise a capture moiety (i.e., pathogen binding element) that has one or more magnetic particles attached to it.

In certain aspects, methods of the invention involve obtaining a heterogeneous sample including a pathogen, exposing the sample to a cocktail including a plurality of sets of magnetic particles, members of each set being conjugated to a capture moiety specific for a pathogen, and separating particle bound pathogen from other components in the sample. Methods of the invention may further involve characterizing the pathogen. Characterizing may include identifying the pathogen by any technique known in the art. Exemplary techniques include sequencing nucleic acid derived from the pathogen or amplifying the nucleic acid.

Any class of capture moiety capable of specifically binding to a pathogen is suitable for use in methods and compositions of the invention. Suitable classes of capture moieties include, e.g., antibodies, lectins, bacteriophages, antimicrobial agents, and oligonucleotides. Classes of capture moieties may include one or more different types of that class, e.g. an antibody class may include one or more types of antibodies that are specific to different pathogens. The antibodies conjugated to the particles may be either monoclonal or polyclonal antibodies. Methods of the invention may be used to isolate one or more pathogens from heterogeneous sample. In particular embodiments, the heterogeneous sample is a blood sample.

According to certain aspects, compositions of the invention include a plurality of sets of magnetic particles, in which each set is conjugated with capture moieties having different specificities for different pathogens. The capture moieties conjugated to the magnetic particles may be of the same class or different class. For example, one set of capture moieties may be antibodies specific to a first pathogen, and the other set of capture moieties may be other antibodies specific to a second pathogen. In another example, one set of capture moieties may be antibodies specific to a first pathogen, and the other set of capture moieties may be lectins specific to a second pathogen.

In other aspects, compositions of the invention include at least one magnetic particle that is conjugated to at least two sets of capture moieties, in which each set of capture moieties is specific for a different pathogen. The at least two sets of capture moieties conjugated to a magnetic particle may be of the same class or different classes. For example, a magnetic particle may have two or more antibodies specific to different pathogens. In another example, a magnetic particle may be conjugated to an antibody specific to a pathogen and a lectin specific to a different pathogen.

Compositions of the invention may be provided such that each set of particles conjugated to capture moieties is present at a concentration designed for detection of a specific pathogen in the sample. In certain embodiments, all of the sets are provided at the same concentration. Alternatively, the sets are provided at different concentrations. For example, the concentration ratio of one set of capture moieties relative to a second set of capture moieties is at a ratio of 50:50. In other embodiments, the concentration ratio ranges from 1:99 to 99:1.

To facilitate detection of the different sets of pathogen/magnetic particle complexes the particles may be differently labeled. Any detectable label may be used with compositions of the invention, such as fluorescent labels, radiolabels, enzymatic labels, and others. In particular embodiments, the detectable label is an optically-detectable label, such as a fluorescent label. Exemplary fluorescent labels include Cy3, Cy5, Atto, cyanine, rhodamine, fluorescien, coumarin, BODIPY, alexa, and conjugated multi-dyes.

Methods of the invention may be used to isolate one or more pathogens from a sample. Methods of the invention may be used to isolate only gram positive bacteria from a sample. Alternatively, methods of the invention may be used to isolate only gram negative bacteria from a sample. In certain embodiments, methods of the invention are used to isolate both gram positive and gram negative bacteria from a sample.

In still other embodiments, methods isolate specific pathogens, such as bacteria or fungi, from a sample. Exemplary fungal species that may be captured by methods of the invention include species from the *Candida* genus, *Aspergillus* genus, and *Cryptococcus* genus. In particular embodiments, the specific fungal species include *C. albicans, C. glabarata, C. parapsilosis, C. tropicalis, C. krusei, Cryptococcus neoformans, Cryptococcus gattii*. Exemplary bacteria that may be captured and isolated by methods of the invention include bacteria of the *Escherichia* genus, *Listeria* genus, *Clostridium* genus, Enterobacteriaceae family, *Mycobacterium* genus, *Shigella* genus, *Borrelia* genus, *Campylobacter* genus, *Bacillus* genus, *Salmonella* genus, *Enterococcus* genus, *Streptococcus* genus (such as *Pneumococcus*), *Acinetobacter* genus, *Strenotrophomonas* genus, *Pseudomonas* genus, *Neisseria* genus, and *Haemophilus* genus. The method may also be used to detect the mecA gene, which is a bacterial gene associated with antibiotic resistance.

Methods of the invention are not limited to isolating pathogens from a body fluid. Methods of the invention may be designed to isolate other types of target analytes, such as bacteria, fungi, protein, a cell, a virus, a nucleic acid, a receptor, a ligand, or any molecule known in the art.

Compositions used in methods of the invention may use any type of magnetic particle. Magnetic particles generally fall into two broad categories. The first category includes particles that are permanently magnetizable, or ferromagnetic; and the second category includes particles that demonstrate bulk magnetic behavior only when subjected to a magnetic field. The latter are referred to as magnetically responsive particles. Materials displaying magnetically responsive behavior are sometimes described as superparamagnetic. However, materials exhibiting bulk ferromagnetic properties, e.g., magnetic iron oxide, may be characterized as superparamagnetic when provided in crystals of about 30 nm or less in diameter. Larger crystals of ferromagnetic materials, by contrast, retain permanent magnet characteristics after exposure to a magnetic field and tend to aggregate thereafter due to strong particle-particle interaction. In certain embodiments, the particles are superparamagnetic particles. In other embodiments, the magnetic particles include at least 70% superparamagnetic particles by weight. In certain embodiments, the superparamagnetic particles are from about 100 nm to about 250 nm in diameter. In certain embodiments, the magnetic particle is an iron-containing magnetic particle. In other embodiments, the magnetic particle includes iron oxide or iron platinum.

Another aspect of the invention provides methods for isolating pathogen from a heterogeneous sample, that involve labeling pathogen from a biological sample with a cocktail including a plurality of sets of magnetic particles, members of each set being conjugated to an antibody specific for a pathogen, exposing the sample to a magnetic field to isolate pathogen conjugated to the particles, and isolating particle bound pathogen from other components of the sample. Methods of the invention may further involve eluting pathogen from the particles. Methods of the invention may further involve characterizing the pathogen. Characterizing may include identifying the pathogen by any technique known in the art. Exemplary techniques include sequencing nucleic acid derived from the pathogen or amplifying the nucleic acid.

DETAILED DESCRIPTION

The invention generally relates to methods of using compositions that include sets of magnetic particles, members of each set being conjugated to an antibody specific for a pathogen, and magnets to isolate a pathogen from a body fluid sample. Certain fundamental technologies and principles are associated with binding magnetic materials to target entities and subsequently separating by use of magnet fields and gradients. Such fundamental technologies and principles are known in the art and have been previously described, such as those described in Janeway (Immunobiology, $6^{th}$ edition, Garland Science Publishing), the content of which is incorporated by reference herein in its entirety. While some techniques are described exemplifying the isolation and capture of bacteria, one skilled in the art would readily recognize that the techniques are generally applicable to all pathogens including fungi.

Composition used in methods of the invention may use any type of magnetic particle. Production of magnetic particles and particles for use with the invention are known in the art. See for example Giaever (U.S. Pat. No. 3,970,518), Senyi et al. (U.S. Pat. No. 4,230,685), Dodin et al. (U.S. Pat. No. 4,677,055), Whitehead et al. (U.S. Pat. No. 4,695,393), Benjamin et al. (U.S. Pat. No. 5,695,946), Giaever (U.S. Pat. No. 4,018,886), Rembaum (U.S. Pat. No. 4,267,234), Molday (U.S. Pat. No. 4,452,773), Whitehead et al. (U.S. Pat. No. 4,554,088), Forrest (U.S. Pat. No. 4,659,678), Liberti et al. (U.S. Pat. No. 5,186,827), Own et al. (U.S. Pat. No. 4,795,698), and Liberti et al. (WO 91/02811), the content of each of which is incorporated by reference herein in its entirety.

Magnetic particles generally fall into two broad categories. The first category includes particles that are permanently magnetizable, or ferromagnetic; and the second category includes particles that demonstrate bulk magnetic behavior only when subjected to a magnetic field. The latter are referred to as magnetically responsive particles. Materials displaying magnetically responsive behavior are sometimes described as superparamagnetic. However, materials exhibiting bulk ferromagnetic properties, e.g., magnetic iron oxide, may be characterized as superparamagnetic when provided in crystals of about 30 nm or less in diameter. Larger crystals of ferromagnetic materials, by contrast, retain permanent magnet characteristics after exposure to a magnetic field and tend to aggregate thereafter due to strong particle-particle interaction. In certain embodiments, the particles are superparamagnetic particles. In certain embodiments, the magnetic particle is an iron containing magnetic particle. In other embodiments, the magnetic particle includes iron oxide or iron platinum.

In certain embodiments, the magnetic particles include at least about 10% superparamagnetic particles by weight, at least about 20% superparamagnetic particles by weight, at least about 30% superparamagnetic particles by weight, at least about 40% superparamagnetic particles by weight, at least about 50% superparamagnetic particles by weight, at least about 60% superparamagnetic particles by weight, at least about 70% superparamagnetic particles by weight, at least about 80% superparamagnetic particles by weight, at least about 90% superparamagnetic particles by weight, at least about 95% superparamagnetic particles by weight, or at least about 99% superparamagnetic particles by weight. In a particular embodiment, the magnetic particles include at least about 70% superparamagnetic particles by weight.

In certain embodiments, the superparamagnetic particles are less than 100 nm in diameter. In other embodiments, the superparamagnetic particles are about 150 nm in diameter, are about 200 nm in diameter, are about 250 nm in diameter, are about 300 nm in diameter, are about 350 nm in diameter, are about 400 nm in diameter, are about 500 nm in diameter, or are about 1000 nm in diameter. In a particular embodiment, the superparamagnetic particles are from about 100 nm to about 250 nm in diameter.

In certain embodiments, the particles are particles (e.g., nanoparticles) that incorporate magnetic materials, or magnetic materials that have been functionalized, or other configurations as are known in the art. In certain embodiments, nanoparticles may be used that include a polymer material that incorporates magnetic material(s), such as nanometal material(s). When those nanometal material(s) or crystal(s), such as $Fe_3O_4$, are superparamagnetic, they may provide advantageous properties, such as being capable of being magnetized by an external magnetic field, and demagnetized when the external magnetic field has been removed. This may be advantageous for facilitating sample transport into and away from an area where the sample is being processed without undue particle aggregation.

One or more or many different nanometal(s) may be employed, such as $Fe_3O_4$, FePt, or Fe, in a core-shell configuration to provide stability, and/or various others as may be known in the art. In many applications, it may be advantageous to have a nanometal having as high a saturated moment per volume as possible, as this may maximize gradient related forces, and/or may enhance a signal associated with the presence of the particles. It may also be advantageous to have the volumetric loading in a particle be as high as possible, for the same or similar reason(s). In order to maximize the moment provided by a magnetizable nanometal, a certain saturation field may be provided. For example, for $Fe_3O_4$ superparamagnetic particles, this field may be on the order of about 0.3 T.

The size of the nanometal containing particle may be optimized for a particular application, for example, maximizing moment loaded upon a target, maximizing the number of particles on a target with an acceptable detectability, maximizing desired force-induced motion, and/or maximizing the difference in attached moment between the labeled target and non-specifically bound targets or particle aggregates or individual particles. While maximizing is referenced by example above, other optimizations or alterations are contemplated, such as minimizing or otherwise desirably affecting conditions.

In an exemplary embodiment, a polymer particle containing 80 wt % $Fe_3O_4$ superparamagnetic particles, or for example, 90 wt % or higher superparamagnetic particles, is produced by encapsulating superparamagnetic particles with a polymer coating to produce a particle having a diameter of about 250 nm.

Compositions of the invention include sets of a plurality of magnetic particles specific to different targets of interest (e.g., pathogens). Each set of magnetic particles has a target-specific binding moiety (capture moiety) that allows for each set to specifically bind the target of interest in the heterogeneous sample. Exemplary classes of capture moieties include oligonucleotides (including nucleic acid probes), proteins, ligands, lectins, antibodies, aptamers, bactertiophages, host innate immunity biomarkers (e.g., CD14), host defense peptides (e.g., defensins), bacteriocins (e.g., pyocins), and receptors. The capture moiety may be specific to a certain species within a genus of pathogen, or the capture moiety may be generally specific to several species within or the entire genus of pathogen. A class of capture moieties may include one or more different types of that class, e.g. an antibody specific to one pathogen and an antibody specific to another pathogen. In addition, one set of magnetic particles may be conjugated to a class of capture moieties that are different from a class of capture moieties conjugated to another set. For example, one set of magnetic particles may be conjugated to an antibody specific to a pathogen and another set of magnetic particles may be conjugated to a lectin specific to a different pathogen. The classes and types of capture moieties utilized will depend on the target to be captured and isolated.

In certain embodiments, each magnetic particle of a set is conjugated to at least two different sets of capture moieties specific to different pathogens. That is, one magnetic particle may have two or more capture moieties specific to different pathogens. The two or more capture moieties conjugated to a magnetic particle may be of the same class or different class. For example, a magnetic particle may have two or more antibodies specific to different pathogens. In another example, a magnetic particle may be conjugated to an antibody specific to a pathogen and a lectin specific to a different pathogen.

In particular embodiments, the capture moiety is an antibody, such as an antibody that binds a particular pathogen. General methodologies for antibody production, including criteria to be considered when choosing an animal for the production of antisera, are described in Harlow et al. (Antibodies, Cold Spring Harbor Laboratory, pp. 93-117, 1988). For example, an animal of suitable size such as goats, dogs, sheep, mice, or camels are immunized by administration of an amount of immunogen, such the target bacteria, effective to produce an immune response. An exemplary protocol is as follows. The animal is injected with 100 milligrams of antigen resuspended in adjuvant, for example Freund's complete adjuvant, dependent on the size of the animal, followed three weeks later with a subcutaneous injection of 100 micrograms to 100 milligrams of immunogen with adjuvant dependent on the size of the animal, for example Freund's incomplete adjuvant. Additional subcutaneous or intraperitoneal injections every two weeks with adjuvant, for example Freund's incomplete adjuvant, are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing protein G resin or target-specific affinity resin.

Polyclonal antibodies, monoclonal antibodies, or both can be conjugated to magnetic particles in accordance with compositions and methods of the invention. Polyclonal antibodies are antibodies that are secreted by different B cell lineages, and are a collection of immunoglobulin molecules that react against a specific antigen, each identifying a different epitope. Thus, polyclonal antibodies recognize against *Listeria* are provided in Skjerve et al. (Appl. Env. Microbiol. 56:3478, 1990). Immunomagnetic particles against *Escherichia* coli are provided in Lund et al. (J. Clin. Microbiol. 29:2259, 1991).

In certain embodiments, the target-specific binding moiety is a lectin. Lectins are sugar-binding proteins that are highly specific for their sugar moieties. Exemplary lectins that may be used as target-specific binding moieties include Concanavalin (ConA), Wheat Germ Extract WGA). Lectins that specifically bind to bacteria and fungi are known, see, e.g. Stoddart, R. W., and B. M. Herbertson. "The use of fluorescein-labelled lectins in the detection and identification of fungi pathogenic for man: a preliminary study." Journal of medical microbiology 11.3 (1978): 315-324; and U.S. Pat. No. 5,004,699. In addition, other lectins that have pathogen-binding properties are shown in Table 1 below.

TABLE 1

Lectins with Carbohydrate Specificity

| Lectin | Source | Carbohydrate Specificity |
|---|---|---|
| AMA | *Arum maculatum* (AMA) from 'lords and ladies' flower | Mannose |
| ASA | *Allium sativum* (ASA) from garlic | Mannose |
| Con-A | *Canavalia ensiformis* (Con-A) from jack bean | α-D-Mannose, α-D-Glucose, branched mannose |
| GS-II | *Griffonia simplicoflia* (GS-II) from shrub GS | Terminal α- or β-N-Acetylglucosamine |
| HHA | *Hippeastrum* hybrid (HHA) from amaryllis | Mannose (int and term residues) |
| IRA | *Iris hybric* (IRA) from Dutch Iris | N-Acetyl-D-Galactosamine |
| LEA | *Lycopersicon esculentum* (LEA) from tomato | β(1,4)-linked N-Acetylglucosamine |
| LPA | *Limulus polyphemus* (LPA) from horseshoe crab | Sialic Acid (N-Acetylneuraminic acid) |
| MIA | *Mangidera indica* (MIA) from mango | Exact specificity unknown |
| PAA | *Perseau americana* (PAA) from avocado | Exact specificity unknown |
| WGA | *Triticum vulgaris* (WGA) from Wheat Germ | (GlcNAc-β-(1,4)-GlcNAc)1-4>β-GlcNAc>Neu5Ac |
| WGA-S | Succinyl *Triticum vulgare* (WGA-S) from wheat germ | (GlcNAc-β-(1,4)-GlcNAc)1-4>β-GlcNAc>Neu5Ac | multiple epitopes on any one antigen. Polyclonal antibodies are useful in identifying homologous pathogens, and allow for general isolation and capture of a range of species. In contrast, monoclonal antibodies are constructed from one cell line, and recognize only one epitope on an antigen. Monoclonal antibodies are more specific, and typically only bind to the epitope of the specific target cell (e.g. less likely to bind to a range of species).

The technique of in vitro immunization of human lymphocytes is used to generate monoclonal antibodies. Techniques for in vitro immunization of human lymphocytes are well known to those skilled in the art. See, e.g., Inai, et al., Histochemistry, 99(5):335 362, May 1993; Mulder, et al., Hum. Immunol., 36(3):186 192, 1993; Harada, et al., J. Oral Pathol. Med., 22(4):145 152, 1993; Stauber, et al., J. Immunol. Methods, 161(2):157 168, 1993; and Venkateswaran, et al., Hybridoma, 11(6) 729 739, 1992. These techniques can be used to produce antigen-reactive monoclonal antibodies, including antigen-specific IgG, and IgM monoclonal antibodies.

Any antibody or fragment thereof having affinity and specific for the bacteria of interest is within the scope of the invention provided herein. Immunomagnetic particles against *Salmonella* are provided in Vermunt et al. (J. Appl. Bact. 72:112, 1992). Immunomagnetic particles against *Staphylococcus aureus* are provided in Johne et al. (J. Clin. Microbiol. 27:1631, 1989). Immunomagnetic particles Capture moieties suitable for use in methods of the invention may also include a nucleic acid ligand (aptamer). A nucleic acid ligand (aptamer) is a nucleic acid macromolecule (e.g., DNA or RNA) that binds tightly to a specific molecular target. Like all nucleic acids, a particular nucleic acid ligand may be described by a linear sequence of nucleotides (A, U, T, C and G), typically 15-40 nucleotides long. In solution, the chain of nucleotides forms intramolecular interactions that fold the molecule into a complex three-dimensional shape. The shape of the nucleic acid ligand allows it to bind tightly against the surface of its target molecule. In addition to exhibiting remarkable specificity, nucleic acid ligands generally bind their targets with very high affinity, e.g., the majority of anti-protein nucleic acid ligands have equilibrium dissociation constants in the picomolar to low nanomolar range.

Nucleic acid ligands are generally discovered using an in vitro selection process referred to as SELEX (Systematic Evolution of Ligands by EXponential enrichment). See for example Gold et al. (U.S. Pat. No. 5,270,163). SELEX is an iterative process used to identify a nucleic acid ligand to a chosen molecular target from a large pool of nucleic acids. The process relies on standard molecular biological techniques, using multiple rounds of selection, partitioning, and amplification of nucleic acid ligands to resolve the nucleic acid ligands with the highest affinity for a target molecule.

In addition, the capture moiety may be a nucleic acid probe, typically an oligonucleotide, that specifically binds to a target nucleic acid sequence. A probe is generally a single-stranded nucleic acid sequence complementary to some degree to a nucleic acid sequence sought to be detected ("target sequence"). A probe may be labeled with a reporter group moiety such as a radioisotope, a fluorescent or chemiluminescent moiety, or with an enzyme or other ligand which can be used for detection. Standard techniques are used for nucleic acid and peptide synthesis. These molecular biological techniques may be performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y.,). Synthesis of complementary DNA is described in, for example, Nature Methods 2, 151-152 (2005) doi:10.1038/nmeth0205-151. Background descriptions of the use of nucleic acid hybridization to detect particular nucleic acid sequences are given in Kohne, U.S. Pat. No. 4,851,330 issued Jul. 25, 1989, and by Hogan et al., International Patent Application No. PCT/US87/03009, entitled "Nucleic Acid Probes for Detection and/or Quantitation of Non-Viral Organisms," both references hereby incorporated by reference herein. Hogan et al., supra, describe methods for determining the presence of a non-viral organism or a group of non-viral organisms in a sample (e.g., sputum, urine, blood and tissue sections, food, soil and water).

Reporter phages may also be used as a capture moiety. Reporter phages, such as bacteriophages, are typically genetically modified phages used to introduce a gene of interest into a host pathogen. The reporter gene incorporates detectable codes for a fluorescent or substrate dependent colorimetric marker into host pathogen, which allows for subsequent pathogen detection. Bacteriophages used for pathogen detection are described in detail in Singh, Amit, et al. "Bacteriophage based probes for pathogen detection." Analyst 137.15 (2012): 3405-3421.; Dover, Jason E., et al. "Recent advances in peptide probe-based biosensors for detection of infectious agents." Journal of microbiological methods 78.1 (2009): 10-19.

Methods for attaching the target-specific binding moiety to the magnetic particle are known in the art. Coating magnetic particles with antibodies is well known in the art, see for example Harlow et al. (Antibodies, Cold Spring Harbor Laboratory, 1988), Hunter et al. (Immunoassays for Clinical Chemistry, pp. 147-162, eds., Churchill Livingston, Edinborough, 1983), and Stanley (Essentials in Immunology and Serology, Delmar, pp. 152-153, 2002). Such methodology can easily be modified by one of skill in the art to bind other types of target-specific binding moieties to the magnetic particles. Certain types of magnetic particles coated with a functional moiety are commercially available from Sigma-Aldrich (St. Louis, Mo.).

Since each set of particles is conjugated with capture moieties having different specificities for different pathogens, compositions used in methods of the invention may be provided such that each set of capture moiety conjugated particles is present at a concentration designed for detection of a specific pathogen in the sample. In certain embodiments, all of the sets are provided at the same concentration. Alternatively, the sets are provided at different concentrations. For example, compositions may be designed such that sets that bind gram positive bacteria are added to the sample at a concentration of $2 \times 10^9$ particles per/ml, while sets that bind gram negative bacteria are added to the sample at a concentration of $4 \times 10^9$ particles per/ml. Compositions used with methods of the invention are not affected by antibody cross-reactivity. However, in certain embodiments, sets are specifically designed such that there is no cross-reactivity between different antibodies and different sets.

Methods of the invention may be used to isolate only gram positive bacteria from a sample. Alternatively, methods of the invention may be used to isolate only gram negative bacteria from a sample. In certain embodiments, methods of the invention are used to isolate both gram positive and gram negative bacteria from a sample. Such compositions allow for isolation of essentially all bacteria from a sample.

In still other embodiments, compositions used with methods of the invention are designed to isolate specific pathogen from a sample. Typically, the pathogens are fungi (e.g., yeast or other pathogenic fungi) or bacteria. Exemplary fungal species that may be captured by methods of the invention include species from the *Candida* genus, *Aspergillus* genus, and *Cryptococcus* genus. In particular embodiments, the specific fungal species include *C. albicans, C. glabarata, C. parapsilosis, C. tropicalis, C. krusei, Cryptococcus neoformans, Cryptococcus gattii*. Exemplary bacteria that may be captured and isolated by methods of the invention include bacteria of the *Escherichia* genus, *Listeria* genus, *Clostridium* genus, Enterobacteriaceae family, *Mycobacterium* genus, *Shigella* genus, *Borrelia* genus, *Campylobacter* genus, *Bacillus* genus, *Salmonella* genus, *Enterococcus* genus, *Streptococcus* genus (such as *Pneumococcus*), *Acinetobacter* genus, *Strenotrophomonas* genus, *Pseudomonas* genus, *Neisseria* genus, and *Haemophilus* genus. The method may also be used to detect the mecA gene, which is a bacterial gene associated with antibiotic resistance. In addition, the specific species of pathogen selected for capture and isolation may be based on a certain phenotypic characteristic. For example, capture moieties conjugated to a magnetic particle may be designed to capture coagulase-negative *Staphylococcus* species (e.g. species of *Staphylococcus* that inhibit blood clot formation).

The sets of magnetic particles may be mixed together to isolate certain fungi, bacteria, or both. These sets can be mixed together to isolate for example, *E. coli* and *Listeria*; or *E. coli, Listeria*, and *Clostridium*; or *Mycobacterium, Campylobacter, Bacillus, Salmonella*, and *Staphylococcus*, etc. One set may be specific to a certain bacterium and another set may be specific to a certain fungus. Any combination of sets may be used and compositions of the invention will vary depending on the suspected pathogen or pathogens to be isolated. In certain embodiments, compositions include two, three, four, five . . . 10, 20, etc. different sets of magnetic particles conjugated to different pathogens.

In preferred embodiments, sets of magnetic particles conjugated to capture moieties that are specific to different targets within multi-plex detection panel. For example, sets of modified magnetic particles may be chosen to isolate two or more certain pathogens. The two or more certain pathogens chosen may be causal of similar symptoms (e.g. digestive abnormalities), commonly found in the type of body fluid (e.g. stool), or pathogens common to a certain area (e.g. hospital setting). The following tables show exemplary panels of fungal (Table 2) targets and bacterial (Table 3) targets. "Sp" means a target species within a genus, and "Spp" means multiple target species of genus.

TABLE 2

Fungal Panels-Compositions of the invention will include capture moieties bound to magnetic particles specific to each of the targets in the panel.

| Fungi Assay | Target 1 | Target 2 | Target 3 | Target 4 | Target 5 |
|---|---|---|---|---|---|
| Panel A | Species of Candida genus | C. albicans | C. glabrata | C. parapsilosis (or C. tropicalis) | N/A |
| Panel B | Species of Candida genus | C. albicans | C. glabrata | C. parapsilosis/ C. tropicalis | C. krusei |
| Panel C | Species of Candida genus | C. albicans | C. glabrata/ C. krusei | C. parapsilosis/ C. tropicalis | Cryptococcus spp. |
| Panel D | Candida genus | C. albicans/C. parapsilosis/ C. tropicalis | C. glabrata/C. krusei | Aspergillus spp. | Cryptococcus spp. |
| Panel E | Cryptococcus neoformans | C. albicans/C. parapsilosis/ C. tropicalis | C. glabrata/C. krusei | Aspergillus spp. | Cryptococcus gattii |

TABLE 3

Bacteria Panels-Compositions of the invention will include capture moieties bound to magnetic particles specific to each of the targets in the panel.

| Bacteria Assay | Target 1 | Target 2 | Target 3 | Target 4 | Target 5 |
|---|---|---|---|---|---|
| Panel A- Gram Positive Panel | S. aureus | CoNS | mecA | Streptococcus sp./Enterococcocus sp. | N/A |
| Panel B- Gram Negative Panel | Enterobacteriaceae | Pseudomonas aeruginosa | Acinetobacter sp. | Stenotrophomonas maltophilia (or other GNR such as Neisseria, Haemophilus) | N/A |
| Panel C | Staphylococcus sp. | CoNS | Enterobacteriaceae | Pseudomonas aeruginosa | N/A |
| Panel D | Staphylococcus sp. | Enterococcus sp./Streptococcus sp. | E. coli | Pseudomonas aeruginosa | N/A |
| Panel E | Staphylococcus aureus | CoNS | Enterococcus sp./Streptococcus sp. | Enterobacteriaceae | N/A |
| Panel F | Staphylococcus sp. | Enterococcus sp./Streptococcus sp. | Enterobacteriaceae | Candida spp. | N/A |
| Panel G- Gram Positive Panel | S. aureus | CoNS | mecA | Streptococcus sp. | Enterococcocus sp. |
| Panel H- Gram Negative Panel | Enterobacteriaceae | Pseudomonas aeruginosa | Acinetobacter sp. | Stenotrophomonas maltophilia | Neisseria meningitidis |
| Panel I | Staphylococcus sp. | Enterococcus sp. | Streptococcus sp. | Enterobacteriaceae | Pseudomonas aeruginosa |
| Panel J | Staphylococcus sp. | Enterococcus sp. | Streptococcus sp. | E. coli | Pseudomonas aeruginosa |
| Panel K | Staphylococcus aureus | CoNS | Enterococcus sp./Streptococcus sp. | Enterobacteriaceae | Pseudomonas aeruginosa |
| Panel L | Staphylococcus sp. | Enterococcus sp./Streptococcus sp. | Enterobacteriaceae | Pseudomonas aeruginosa | Acinetobacter sp. |

In certain embodiments, compositions of the invention include at least one set magnetic particles conjugated to a capture moiety specific to an internal control (IC). For example, an IC detectable marker may be placed into a clinical sample suspected of containing a pathogen. For detection of the pathogen, a plurality of sets of magnetic particles are introduced to that clinical sample, in which at least one set is conjugated to a capture moiety designed to bind the IC detectable marker and one or more other sets are conjugated to capture moieties designed to bind to the suspected pathogens. When the assay is conducted to capture and isolate the pathogen, the presence or absence of the IC detectable marker indicates whether the assay properly separated the marker from the sample. That is, the introduction of a detectable marker allows one to determine whether the sets of magnetic particles conjugated to capture moieties are properly capturing or isolating the target pathogens that are present within the fluid. This is important to distinguish between a failed assay (i.e. failure to identify a target pathogen present in the sample) and a positive assay (i.e. positively determining the absence of a target pathogen). The presence of the marker indicates that the assay worked properly; and thus any detection of pathogen (or the absence of the pathogen) is accurate and not the result of a failed assay. Use of IC detectable markers is described in more detail in co-owned and co-assigned U.S. Provisional Application No. 61/739,577, filed Dec. 18, 2012. The panels listed in Tables 2 and 3 above may include the addition of an IC detectable marker inserted into the sample, and the sets of magnetic particles would include sets conjugated to capture moieties specific to targets listed in the panel as well as the internal control.

Methods of the invention that utilize the internal control involve obtaining a sample suspected of containing a pathogen and introducing a detectable maker into the sample. An assay is conducted to detect the suspected pathogen and the detectable marker in the sample using a plurality of sets of magnetic particles (as described herein). Members of at least one set of magnetic particles are conjugated to binding entity specific to a pathogen, and members of at least one set of magnetic particles are conjugated to a binding entity specific to the detectable marker. After the conducting step, the presence of absence of the marker in the sample is determined. Based on the presence or absence of the detectable marker, a determination is made about the presence or absence of targets in the sample. The presence of the marker indicates that the assay worked properly; and thus any detection of pathogen (or the absence of pathogen) is accurate and not the result of a failed assay.

Any detectable marker may be used for an internal control. In certain embodiments, the IC detectable marker may be a microbe, including a viable or nonviable microbe. In addition, the IC detectable marker can be sufficiently similar to the target such that the assay performs functionally in the same manner for the detectable marker and the target. The detectable marker may be labeled or otherwise modified to allow for their differentiation from targets originally present in the sample. For example, but not by way of limitation, the detectable marker can be genetically modified so as to express a fluorescent protein, or alternatively, the detectable marker could be pre-stained with a persistent stain to allow their differentiation from microbes that are originally present in the fluid composition. In addition, the detectable marker may be chosen based a chromogen dye specific reaction to the presence of the detectable marker.

Capture of a wide range of target microorganisms simultaneously can be achieved by utilizing antibodies specific to target class, such as pan-Gram-positive antibodies, pan-Gran-negative antibodies or antibodies specific to a subset of organisms of a certain class. Further, expanded reactivity can be achieved by mixing particles of different reactivity. It was shown in our experiments that addition of high concentration of non-specific particles does not interfere with the capture efficiency of target-specific particles. Similarly, several different particle preparations can be combined to allow for the efficient capture of desired pathogens. In certain embodiments the particles can be utilized at a concentration between $1 \times 10^8$ and $5 \times 10^{10}$ particles/mL.

In certain embodiments the expanded coverage can be provided by mixing antibodies with different specificity before attaching them to magnetic particles. Purified antibodies can be mixed and conjugated to activated magnetic particle using standard methods known in the art.

To facilitate detection of the different sets of pathogen/magnetic particle complexes the particles may be differently labeled. Any detectable label may be used with compositions of the invention, such as fluorescent labels, radiolabels, enzymatic labels, and others. The detectable label may be directly or indirectly detectable. In certain embodiments, the exact label may be selected based, at least in part, on the particular type of detection method used. Exemplary detection methods include radioactive detection, optical absorbance detection, e.g., UV-visible absorbance detection, optical emission detection, e.g., fluorescence; phosphorescence or chemiluminescence; Raman scattering. Preferred labels include optically-detectable labels, such as fluorescent labels. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Atto dyes, Cy3; Cy5; Cy5.5; Cy7; IRD 700; IRD 800; La Jolta Blue; phthalo cyanine; and naphthalo cyanine. Preferred fluorescent labels are cyanine-3 and cyanine-5. Labels other than fluorescent labels are contemplated by the invention, including other optically-detectable labels. Methods of linking fluorescent labels to magnetic particles or antibodies are known in the art.

Methods of the invention may be used to isolate pathogen from any heterogeneous sample. In particular embodiments, methods of the invention isolate a pathogen from body fluid.

A body fluid refers to a liquid material derived from, for example, a human or other mammal. Such body fluids include, but are not limited to, mucus, blood, plasma, serum, serum derivatives, bile, phlegm, saliva, sweat, amniotic fluid, mammary fluid, urine, sputum, and cerebrospinal fluid (CSF), such as lumbar or ventricular CSF. A body fluid may also be a fine needle aspirate. A body fluid also may be media containing cells or biological material.

In particular embodiments, the fluid is blood. Methods of the invention allow for bacteria in a blood sample to be isolated and detected at a level as low as or even lower than 1 CFU/ml. Blood may be collected in a container, such as a blood collection tube (e.g., VACUTAINER, test tube specifically designed for venipuncture, commercially available from Becton, Dickinson and company). In certain embodiments, a solution is added that prevents or reduces aggregation of endogenous aggregating factors, such as heparin in the case of blood.

The blood sample is then mixed with compositions as described above to generate a mixture that is allowed to incubate such that the compositions bind to at least one bacterium in the blood sample. The type or types of bacteria that will bind compositions of the invention will depend on the design of the composition, i.e., which antibody conjugated particles are used. The mixture is allowed to incubate for a sufficient time to allow for the composition to bind to the pathogen in the blood. The process of binding the composition to the pathogen associates a magnetic moment with the pathogen, and thus allows the pathogen to be manipulated through forces generated by magnetic fields upon the attached magnetic moment.

In general, incubation time will depend on the desired degree of binding between the pathogen and the compositions of the invention (e.g., the amount of moment that would be desirably attached to the pathogen), the amount of moment per target, the amount of time of mixing, the type of mixing, the reagents present to promote the binding and the binding chemistry system that is being employed. Incubation time can be anywhere from about 5 seconds to a few days. Exemplary incubation times range from about 10 seconds to about 2 hours. Binding occurs over a wide range of temperatures, generally between 15° C. and 40° C.

In certain embodiments, a buffer solution is added to the sample along with the compositions of the invention. An exemplary buffer includes Tris(hydroximethyl)-aminomethane hydrochloride at a concentration of about 75 mM. It has been found that the buffer composition, mixing parameters (speed, type of mixing, such as rotation, shaking etc., and temperature) influence binding. It is important to maintain osmolality of the final solution (e.g., blood+buffer) to maintain high label efficiency. In certain embodiments, buffers used in methods of the invention are designed to prevent lysis of blood cells, facilitate efficient binding of targets with magnetic particles and to reduce formation of particle aggregates. It has been found that the buffer solution containing 300 mM NaCl, 75 mM Tris-HCl pH 8.0 and 0.1% Tween 20 meets these design goals.

Without being limited by any particular theory or mechanism of action, it is believed that sodium chloride is mainly responsible for maintaining osmolality of the solution and for the reduction of non-specific binding of magnetic particle through ionic interaction. Tris(hydroximethyl)-aminomethane hydrochloride is a well established buffer compound frequently used in biology to maintain pH of a solution. It has been found that 75 mM concentration is beneficial and sufficient for high binding efficiency. Likewise, Tween 20 is widely used as a mild detergent to decrease nonspecific attachment due to hydrophobic interactions. Various assays use Tween 20 at concentrations ranging from 0.01% to 1%. The 0.1% concentration appears to be optimal for the efficient labeling of bacteria, while maintaining blood cells intact.

Additional compounds can be used to modulate the capture efficiency by blocking or reducing non-specific interaction with blood components and either magnetic particles or pathogens. For example, chelating compounds, such as EDTA or EGTA, can be used to prevent or minimize interactions that are sensitive to the presence of $Ca^{2+}$ or $Mg^{2+}$ ions.

An alternative approach to achieve high binding efficiency while reducing time required for the binding step is to use static mixer, or other mixing devices that provide efficient mixing of viscous samples at high flow rates, such as at or around 5 mL/min. In one embodiment, the sample is mixed with binding buffer in ratio of, or about, 1:1, using a mixing interface connector. The diluted sample then flows through a mixing interface connector where it is mixed with target-specific nanoparticles. Additional mixing interface connectors providing mixing of sample and antigen-specific nanoparticles can be attached downstream to improve binding efficiency. The combined flow rate of the labeled sample is selected such that it is compatible with downstream processing.

After binding of the compositions to the pathogen in the sample to form pathogen/magnetic particle complexes, a magnetic field is applied to the mixture to capture the complexes on a surface. Components of the mixture that are not bound to magnetic particles will not be affected by the magnetic field and will remain free in the mixture. Methods and apparatuses for separating target/magnetic particle complexes from other components of a mixture are known in the art. For example, a steel mesh may be coupled to a magnet, a linear channel or channels may be configured with adjacent magnets, or quadrupole magnets with annular flow may be used. Other methods and apparatuses for separating target/magnetic particle complexes from other components of a mixture are shown in Rao et al. (U.S. Pat. No. 6,551,843), Liberti et al. (U.S. Pat. No. 5,622,831), Hatch et al. (U.S. Pat. No. 6,514,415), Benjamin et al. (U.S. Pat. No. 5,695,946), Liberti et al. (U.S. Pat. No. 5,186,827), Wang et al. (U.S. Pat. No. 5,541,072), Liberti et al. (U.S. Pat. No. 5,466,574), and Terstappen et al. (U.S. Pat. No. 6,623,983), the content of each of which is incorporated by reference herein in its entirety.

In certain embodiments, the magnetic capture is achieved at high efficiency by utilizing a flow-through capture cell with a number of strong rare earth bar magnets placed perpendicular to the flow of the sample. When using a flow chamber with flow path cross-section 0.5 mm×20 mm (h×w) and 7 bar NdFeB magnets, the flow rate could be as high as 5 mL/min or more, while achieving capture efficiency close to 100%.

The above described type of magnetic separation produces efficient capture of a target analyte and the removal of a majority of the remaining components of a sample mixture. However, such a process produces a sample that contains a very high percent of magnetic particles that are not bound to target analytes because the magnetic particles are typically added in excess, as well as non-specific target entities. Non-specific target entities may for example be bound at a much lower efficiency, for example 1% of the surface area, while a target of interest might be loaded at 50% or nearly 100% of the available surface area or available antigenic cites. However, even 1% loading may be sufficient to impart force necessary for trapping in a magnetic gradient flow cell or sample chamber.

For example, in the case of immunomagnetic binding of bacteria or fungi in a blood sample, the sample may include: bound targets at a concentration of about 1/mL or a concentration less than about $10^6$/mL; background particles at a concentration of about $10^7$/ml to about $10^{10}$/ml; and non-specific targets at a concentration of about 10/ml to about $10^5$/ml.

The presence of magnetic particles that are not bound to target analytes and non-specific target entities on the surface that includes the target/magnetic particle complexes interferes with the ability to successfully detect the target of interest. The magnetic capture of the resulting mix, and close contact of magnetic particles with each other and bound targets, result in the formation of aggregate that is hard to dispense and which might be resistant or inadequate for subsequent processing or analysis steps. In order to remove magnetic particles that are not bound to target analytes and non-specific target entities, the surface may be washed with a wash solution that reduces particle aggregation, thereby isolating target/magnetic particle complexes from the magnetic particles that are not bound to target analytes and non-specific target entities. The wash solution minimizes the formation of the aggregates.

Any wash solution that imparts a net negative charge to the magnetic particle that is not sufficient to disrupt interaction between the target-specific moiety of the magnetic particle and the target analyte may be used. Without being limited by any particular theory or mechanism of action, it is believed that attachment of the negatively charged molecules in the wash solution to magnetic particles provides net negative charge to the particles and facilitates dispersal of non-specifically aggregated particles. At the same time, the net negative charge is not sufficient to disrupt strong interaction between the target-specific moiety of the magnetic particle and the target analyte (e.g., an antibody-antigen interaction). Exemplary solutions include heparin, Tris-HCl, Tris-borate-EDTA (TBE), Tris-acetate-EDTA (TAE), Tris-cacodylate, HEPES (4-(2-hydroxyethyl)-1-piperazineethanesulphonic acid), PBS (phosphate buffered saline), PIPES (piperazine-N,N'-bis(2-ethanesulfonic acid), MES (2-N-morpholino)ethanesulfonic acid), Tricine (N-(Tri (hydroximethyl)methyl)glycine), and similar buffering agents. In certain embodiments, only a single wash cycle is performed. In other embodiments, more than one wash cycle is performed.

In particular embodiments, the wash solution includes heparin. For embodiments in which the body fluid sample is blood, the heparin also reduces probability of clotting of blood components after magnetic capture. The bound targets are washed with heparin-containing buffer 1-3 times to remove blood components and to reduce formation of aggregates.

In addition to the above described methods, compositions of the invention may be applied or adapted to other methods for isolating pathogens using other methods, including the methods described in co-owned U.S. publication nos. 2011/0263833, 2011/0262925, 2011/0262932, 2011/0262933, 2011/0262926, and 2011/0262927, the entireties of which are incorporated by reference.

Once the target/magnetic particle complexes are isolated, the target may be analyzed by a multitude of existing technologies, such as miniature NMR, Polymerase Chain Reaction (e.g., PCR, digital PCR, real-time or quantitative PCR), Enzyme Immunoassay (EIA), mass spectrometry, fluorescent labeling and visualization using microscopic observation, fluorescent in situ hybridization (FISH), growth-based antibiotic sensitivity tests, and variety of other methods that may be conducted with purified target without significant contamination from other sample components. In one embodiment, isolated bacteria are eluted from the magnetic particles and are lysed with a chaotropic solution, and DNA is bound to DNA extraction resin. After washing of the resin, the bacterial DNA is eluted and used in quantitative RT-PCR to detect the presence of a specific species, and/or, subclasses of bacteria.

In another embodiment, captured bacteria is removed from the magnetic particles to which they are bound and the processed sample is mixed with fluorescent labeled antibodies specific to the bacteria or fluorescent Gram stain. After incubation, the reaction mixture is filtered through 0.2 μm to 1.0 μm filter to capture labeled bacteria while allowing majority of free particles and fluorescent labels to pass through the filter. Bacteria is visualized on the filter using microscopic techniques, e.g. direct microscopic observation, laser scanning or other automated methods of image capture. The presence of bacteria is detected through image analysis. After the positive detection by visual techniques, the bacteria can be further characterized using PCR or genomic methods.

Detection of pathogens of interest can be performed by use of nucleic acid probes following procedures which are known in the art. Suitable procedures for detection of pathogens using nucleic acid probes are described, for example, in Stackebrandt et al. (U.S. Pat. No. 5,089,386), King et al. (WO 90/08841), Foster et al. (WO 92/15883), and Cossart et al. (WO 89/06699), each of which is hereby incorporated by reference.

A suitable nucleic acid probe assay generally includes sample treatment and lysis, hybridization with selected probe(s), hybrid capture, and detection. Lysis of the pathogens (e.g. bacteria or fungi) is necessary to release the nucleic acid for the probes. The nucleic acid target molecules are released by treatment with any of a number of lysis agents, including alkali (such as NaOH), guanidine salts (such as guanidine thiocyanate), enzymes (such as lysozyme, mutanolysin and proteinase K), and detergents. Lysis of the pathogen, therefore, releases both DNA and RNA, particularly ribosomal RNA and chromosomal DNA both of which can be utilized as the target molecules with appropriate selection of a suitable probe. Use of rRNA as the target molecule(s), may be advantageous because rRNAs constitute a significant component of cellular mass, thereby providing an abundance of target molecules. The use of rRNA probes also enhances specificity for the bacteria of interest, that is, positive detection without undesirable cross-reactivity which can lead to false positives or false detection.

Hybridization includes addition of the specific nucleic acid probes. In general, hybridization is the procedure by which two partially or completely complementary nucleic acids are combined, under defined reaction conditions, in an anti-parallel fashion to form specific and stable hydrogen bonds. The selection or stringency of the hybridization/reaction conditions is defined by the length and base composition of the probe/target duplex, as well as by the level and geometry of mis-pairing between the two nucleic acid strands. Stringency is also governed by such reaction parameters as temperature, types and concentrations of denaturing agents present and the type and concentration of ionic species present in the hybridization solution.

The hybridization phase of the nucleic acid probe assay is performed with a single selected probe or with a combination of two, three or more probes. Probes are selected having sequences which are homologous to unique nucleic acid sequences of the target organism. In general, a first capture probe is utilized to capture formed hybrid molecules. The hybrid molecule is then detected by use of antibody reaction or by use of a second detector probe which may be labelled with a radioisotope (such as phosphorus-32) or a fluorescent label (such as fluorescein) or chemiluminescent label.

Detection of pathogen of interest can also be performed by use of PCR techniques. A suitable PCR technique is described, for example, in Verhoef et al. (WO 92/08805). Such protocols may be applied directly to the pathogen captured on the magnetic particles. The pathogen is combined with a lysis buffer and collected nucleic acid target molecules are then utilized as the template for the PCR reaction.

In certain embodiments, nucleic acids derived from the captured pathogen are analyzed in a multiplex reaction in order to rapidly detect two or more pathogens present in the sample. Any multiplex reaction known in the art may be used, such as multiplex ELISA, multiplex sequencing, multiplex probe hybridization, etc. In certain embodiments, multiplex reactions may involve the amplification and quantification of two or more targets in the same reaction volume. Typical multiplex reactions involve PCR, qPCR (real-time PCR), and sequencing.

Multiplex PCR refers to the use of more than one primer pair in a single reaction vessel in order to amplify more than one target sequence. In the case of real-time PCR, more than one primer pair/probe set is utilized. Multiplex PCR allows for simultaneous detection of different targets in the same reaction. The target sequences may be identified by an identifiable label (e.g. fluorescent probe) or by subsequent sequencing. Multiplex real-time PCR uses multiple probe-based assays, in which each assay has a specific probe labeled with a unique fluorescent dye, resulting in different observed colors for each assay. Real-time PCR instruments can discriminate between the fluorescence generated from different dyes. Different probes are labeled with different dyes that each have unique emission spectra. Spectral signals are collected with discrete optics, passed through a series of filter sets, and collected by an array of detectors. Spectral overlap between dyes is corrected by using pure dye spectra to deconvolute the experimental data by matrix algebra. An overview of real-time PCR techniques is described in detail in Elnifro, Elfath M., et al. "Multiplex PCR: optimization and application in diagnostic virology." Clinical Microbiology Reviews 13.4 (2000): 559-570. Multiplex PCR reaction techniques are described in U.S. Publication Nos. 20130059762, and 2005/0026144 as well as Carroll, N. M., E. E. Jaeger, et al. (2000). "Detection of and discrimination between gram-positive and gram-negative bacteria in intraocular samples by using nested PCR." J Clin Microbiol 38(5): 1753-1757, and Klaschik, S., L. E. Lehmann, et al. (2002). "Real-time PCR for detection and differentiation of gram-positive and gram-negative bacteria." J Clin Microbiol 40(11): 4304-4307.

Multiplex sequencing involves the simultaneous sequencing of multiple target sequences in a single sequencing run. Multiplex sequencing allows for differentiation between target sequences of different pathogens in a sample and differentiation between nucleic acid sequences of pooled samples (e.g. differentiate between two or more patient samples). In order to differentiate between target sequences, one or more different barcodes may be introduced to the nucleic acid of a sample. Early multiplex sequencing is described in more detail in G. M. Church in U.S. Pat. No. 4,942,124 and further by G. M. Church and S. Kieffer-Higgins in U.S. Pat. No. 5,149,625. Multiplex sequencing of multiple samples involves sequencing of a plurality of template nucleic acid molecules from different samples at the same time on the same platform by attaching a unique oligonucleotide sequence (i.e., a bar code) to the template nucleic acid molecules from different samples prior to pooling and sequencing of the template molecules. The bar code allows for template nucleic acid sequences from different samples to be differentiated from each other. Once bar coded, template molecules from different samples may be pooled and sequenced at the same time on the same platform. Because the bar code on each template molecule is sequenced as part of the sequencing reaction, the bar code is a component of the sequence data, and thus the sequence data for different samples is always associated with the sample from which it originated. Due to the association in the sequence data, the sequence data from the pooled samples may be separated after sequencing has occurred and correlated back to the sample from which it originated.

Any sequencing technique (for singleplex and multiplex assays) may be utilized to identify isolated pathogens by their nucleic acid extracts. Suitable sequencing techniques include, for example, classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

For detection of the selected pathogens by use of antibodies, isolated pathogen are contacted with antibodies specific to the pathogen of interest. As noted above, either polyclonal or monoclonal antibodies can be utilized, but in either case have affinity for the particular bacteria to be detected. These antibodies, will adhere/bind to material from the specific target bacteria. With respect to labeling of the antibodies, these are labeled either directly or indirectly with labels used in other known immunoassays. Direct labels may include fluorescent, chemiluminescent, bioluminescent, radioactive, metallic, biotin or enzymatic molecules. Methods of combining these labels to antibodies or other macromolecules are well known to those in the art. Examples include the methods of Hijmans, W. et al. (1969), Clin. Exp. Immunol. 4, 457-, for fluorescein isothiocyanate, the method of Goding, J. W. (1976), J. Immunol. Meth. 13, 215-, for tetramethylrhodamine isothiocyanate, and the method of Ingrall, E. (1980), Meth. in Enzymol. 70, 419-439 for enzymes.

These detector antibodies may also be labeled indirectly. In this case the actual detection molecule is attached to a secondary antibody or other molecule with binding affinity for the anti-bacteria cell surface antibody. If a secondary antibody is used it is preferably a general antibody to a class of antibody (IgG and IgM) from the animal species used to raise the anti-bacteria cell surface antibodies. For example, the second antibody may be conjugated to an enzyme, either alkaline phosphatase or to peroxidase. To detect the label, after the bacteria of interest is contacted with the second antibody and washed, the isolated component of the sample is immersed in a solution containing a chromogenic substrate for either alkaline phosphatase or peroxidase. A chromogenic substrate is a compound that can be cleaved by an enzyme to result in the production of some type of detectable signal which only appears when the substrate is cleaved from the base molecule. The chromogenic substrate is colorless, until it reacts with the enzyme, at which time an intensely colored product is made. Thus, material from the bacteria colonies adhered to the membrane sheet will become an intense blue/purple/black color, or brown/red while material from other colonies will remain colorless. Examples of detection molecules include fluorescent substances, such as 4-methylumbelliferyl phosphate, and chromogenic substances, such as 4-nitrophenylphosphate, 3,3', 5,5'-tetramethylbenzidine and 2,2'-azino-di-[3-ethelbenzthiazoliane sulfonate (6)]. In addition to alkaline phosphatase and peroxidase, other useful enzymes include ($\oplus$-galactosidase, $\beta$-glucuronidase, $\alpha$-glucosidase, $\beta$-glucosidase, $\alpha$-mannosidase, galactose oxidase, glucose oxidase and hexokinase.

Detection of bacteria of interest using NMR may be accomplished as follows. In the use of NMR as a detection methodology, in which a sample is delivered to a detector coil centered in a magnet, the target of interest, such as a magnetically labeled bacterium, may be delivered by a fluid medium, such as a fluid substantially composed of water. In such a case, the magnetically labeled target may go from a region of very low magnetic field to a region of high magnetic field, for example, a field produced by an about 1 to about 2 Tesla magnet. In this manner, the sample may traverse a magnetic gradient, on the way into the magnet and on the way out of the magnet. As may be seen via equations 1 and 2 below, the target may experience a force pulling into the magnet in the direction of sample flow on the way into the magnet, and a force into the magnet in the opposite direction of flow on the way out of the magnet. The target may experience a retaining force trapping the target in the magnet if flow is not sufficient to overcome the gradient force.

$$m\text{dot}(del\ B)=F \qquad \text{Equation 1}$$

$$v_t=-F/(6*p*n*r) \qquad \text{Equation 2}$$

where n is the viscosity, r is the particle diameter, F is the vector force, B is the vector field, and m is the vector moment of the particle Magnetic fields on a path into a magnet may be non-uniform in the transverse direction with respect to the flow into the magnet. As such, there may be a transverse force that pulls targets to the side of a container or a conduit that provides the sample flow into the magnet. Generally, the time it takes a target to reach the wall of a conduit is associated with the terminal velocity and is lower with increasing viscosity. The terminal velocity is associated with the drag force, which may be indicative of creep flow in certain cases. In general, it may be advantageous to have a high viscosity to provide a higher drag force such that a target will tend to be carried with the fluid flow through the magnet without being trapped in the magnet or against the conduit walls.

Newtonian fluids have a flow characteristic in a conduit, such as a round pipe, for example, that is parabolic, such that the flow velocity is zero at the wall, and maximal at the center, and having a parabolic characteristic with radius. The velocity decreases in a direction toward the walls, and it is easier to magnetically trap targets near the walls, either with transverse gradients force on the target toward the conduit wall, or in longitudinal gradients sufficient to prevent target flow in the pipe at any position. In order to provide favorable fluid drag force to keep the samples from being trapped in the conduit, it may be advantageous to have a plug flow condition, wherein the fluid velocity is substantially uniform as a function of radial position in the conduit.

When NMR detection is employed in connection with a flowing sample, the detection may be based on a perturbation of the NMR water signal caused by a magnetically labeled target (Sillerud et al., JMR (Journal of Magnetic Resonance), vol. 181, 2006). In such a case, the sample may be excited at time 0, and after some delay, such as about 50 ms or about 100 ms, an acceptable measurement (based on a detected NMR signal) may be produced. Alternatively, such a measurement may be produced immediately after excitation, with the detection continuing for some duration, such as about 50 ms or about 100 ms. It may be advantageous to detect the NMR signal for substantially longer time durations after the excitation.

By way of example, the detection of the NMR signal may continue for a period of about 2 seconds in order to record spectral information at high-resolution. In the case of parabolic or Newtonian flow, the perturbation excited at time 0 is typically smeared because the water around the perturbation source travels at different velocity, depending on radial position in the conduit. In addition, spectral information may be lost due to the smearing or mixing effects of the differential motion of the sample fluid during signal detection. When carrying out an NMR detection application involving a flowing fluid sample, it may be advantageous to provide plug-like sample flow to facilitate desirable NMR contrast and/or desirable NMR signal detection.

Differential motion within a flowing Newtonian fluid may have deleterious effects in certain situations, such as a situation in which spatially localized NMR detection is desired, as in magnetic resonance imaging. In one example, a magnetic object, such as a magnetically labeled bacterium, is flowed through the NMR detector and its presence and location are detected using MRI techniques. The detection may be possible due to the magnetic field of the magnetic object, since this field perturbs the magnetic field of the fluid in the vicinity of the magnetic object. The detection of the magnetic object is improved if the fluid near the object remains near the object. Under these conditions, the magnetic perturbation may be allowed to act longer on any given volume element of the fluid, and the volume elements of the fluid so affected will remain in close spatial proximity. Such a stronger, more localized magnetic perturbation will be more readily detected using NMR or MRI techniques.

If a Newtonian fluid is used to carry the magnetic objects through the detector, the velocity of the fluid volume elements will depend on radial position in the fluid conduit. In such a case, the fluid near a magnetic object will not remain near the magnetic object as the object flows through the detector. The effect of the magnetic perturbation of the object on the surrounding fluid may be smeared out in space, and the strength of the perturbation on any one fluid volume element may be reduced because that element does not stay within range of the perturbation. The weaker, less-well-localized perturbation in the sample fluid may be undetectable using NMR or MRI techniques.

Certain liquids, or mixtures of liquids, exhibit non-parabolic flow profiles in circular conduits. Such fluids may exhibit non-Newtonian flow profiles in other conduit shapes. The use of such a fluid may prove advantageous as the detection fluid in an application employing an NMR-based detection device. Any such advantageous effect may be attributable to high viscosity of the fluid, a plug-like flow profile associated with the fluid, and/or other characteristic(s) attributed to the fluid that facilitate detection. As an example, a shear-thinning fluid of high viscosity may exhibit a flow velocity profile that is substantially uniform across the central regions of the conduit cross-section. The velocity profile of such a fluid may transition to a zero or very low value near or at the walls of the conduit, and this transition region may be confined to a very thin layer near the wall.

Not all fluids, or all fluid mixtures, are compatible with the NMR detection methodology. In one example, a mixture of glycerol and water can provide high viscosity, but the NMR measurement is degraded because separate NMR signals are detected from the water and glycerol molecules making up the mixture. This can undermine the sensitivity of the NMR detector. In another example, the non-water component of the fluid mixture can be chosen to have no NMR signal, which may be achieved by using a perdeuterated fluid component, for example, or using a perfluorinated fluid component. This approach may suffer from the loss of signal intensity since a portion of the fluid in the detection coil does not produce a signal.

Another approach may be to use a secondary fluid component that constitutes only a small fraction of the total fluid mixture. Such a low-concentration secondary fluid component can produce an NMR signal that is of negligible intensity when compared to the signal from the main component of the fluid, which may be water. It may be advantageous to use a low-concentration secondary fluid component that does not produce an NMR signal in the detector. For example, a perfluorinated or perdeuterated secondary fluid component may be used. The fluid mixture used in the NMR detector may include one, two, or more than two secondary components in addition to the main fluid component. The fluid components employed may act in concert to produce the desired fluid flow characteristics, such as high-viscosity and/or plug flow. The fluid components may be useful for providing fluid characteristics that are advantageous for the performance of the NMR detector, for example by providing NMR relaxation times that allow faster operation or higher signal intensities.

A non-Newtonian fluid may provide additional advantages for the detection of objects by NMR or MRI techniques. As one example, the objects being detected may all have substantially the same velocity as they go through the detection coil. This characteristic velocity may allow simpler or more robust algorithms for the analysis of the detection data. As another example, the objects being detected may have fixed, known, and uniform velocity. This may prove advantageous in devices where the position of the detected object at later times is needed, such as in a device that has a sequestration chamber or secondary detection chamber down-stream from the NMR or MRI detection coil, for example.

In an exemplary embodiment, sample delivery into and out of a 1.7 T cylindrical magnet using a fluid delivery medium containing 0.1% to 0.5% Xanthan gum in water was successfully achieved. Such delivery is suitable to provide substantially plug-like flow, high viscosity, such as from about 10 cP to about 3000 cP, and good NMR contrast in relation to water. Xanthan gum acts as a non-Newtonian fluid, having characteristics of a non-Newtonian fluid that are well known in the art, and does not compromise NMR signal characteristics desirable for good detection in a desirable mode of operation.

In certain embodiments, methods of the invention are useful for direct detection of bacteria from blood. Such a process is described here. Sample is collected in sodium heparin tube by venipuncture, acceptable sample volume is about 1 mL to 10 mL. Sample is diluted with binding buffer and superparamagnetic particles having target-specific binding moieties are added to the sample, followed by incubation on a shaking incubator at 37° C. for about 30 min to 120 min. Alternative mixing methods can also be used. In a particular embodiment, sample is pumped through a static mixer, such that reaction buffer and magnetic particles are added to the sample as the sample is pumped through the mixer. This process allows for efficient integration of all components into a single fluidic part, avoids moving parts and separate incubation vessels and reduces incubation time.

Capture of the labeled targets allows for the removal of blood components and reduction of sample volume from 30 mL to 5 mL. The capture is performed in a variety of magnet/flow configurations. In certain embodiments, methods include capture in a sample tube on a shaking platform or capture in a flow-through device at flow rate of 5 mL/min, resulting in total capture time of 6 min.

After capture, the sample is washed with wash buffer including heparin to remove blood components and free particles. The composition of the wash buffer is optimized to reduce aggregation of free particles, while maintaining the integrity of the particle/target complexes.

The detection method is based on a miniature NMR detector tuned to the magnetic resonance of water. When the sample is magnetically homogenous (no bound targets), the NMR signal from water is clearly detectable and strong. The presence of magnetic material in the detector coil disturbs the magnetic field, resulting in reduction in water signal. One of the primary benefits of this detection method is that there is no magnetic background in biological samples which significantly reduces the requirements for stringency of sample processing. In addition, since the detected signal is generated by water, there is a built-in signal amplification which allows for the detection of a single labeled bacterium.

The above described methods for isolating a pathogen may be carried out in a self-contained macrofluidic and/or microfluidic system. Microfluidic substrates or cartridges are known in the art and include one or more chambers, channels, reservoirs, mixers, and traps configured to carry out reactions within the substrate or cartridge. A benefit of microfluidic substrates is that there is no need for external tubing to introduce the various products required for the reaction. Channels of microfluidic system connect and interconnect various components, such as, through holes, slides, foil caps, alignment features, liquid and lyophilized reagent storage chambers, reagent release chambers, pumps, metering chambers, lyophilized cake reconstitution chambers, ultrasonic chambers, joining and mixing chambers, mixing elements such as a mixing paddle and other mixing gear, membrane regions, filtration regions, venting elements, heating elements, magnetic traps/chambers, reaction chambers, waste chambers, membrane regions, thermal transfer regions, anodes, cathodes, and detection regions, drives, plugs, piercing blades, valve lines, valve structures, assembly features such as o-rings, instrument interface regions, cartridge/vessel interfaces, one or more needles associated with the sample interface, optical windows, thermal windows, and detection regions. Pressure sources can be utilized to drive flow and introduce fluid into and out of the microfluidic system. Microfluidic cartridges and microfluidic components can be designed using any technique known in the art, for example the microfluidic fabrication techniques in Lab on a Chip Technology: Fabrication and Microfluidics, Vol. 1, Herold & Rasooley, Caister Academic Press (2009).

An exemplary macrofluidic system and microfluidic system that can be used to carry out methods of the invention is reported in co-owned and co-assigned U.S. Provisional App. No. 61/739,644, filed Dec. 19, 2012, the entirety of which is incorporated by reference.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1: Sample

Blood samples from healthy volunteers were spiked with clinically relevant concentrations of bacteria (1-10 CFU/mL) including both laboratory strains and clinical isolates of the bacterial species most frequently found in bloodstream infections.

Example 2: Antibody Preparation

In order to generate polyclonal, pan-Gram-positive bacteria-specific IgG, a goat was immunized by first administering bacterial antigens suspended in complete Freund's adjuvant intra lymph node, followed by subcutaneous injection of bacterial antigens in incomplete Freund's adjuvant in 2 week intervals. The antigens were prepared for antibody production by growing bacteria to exponential phase ($OD_{600}$=0.4-0.8). Following harvest of the bacteria by centrifugation, the bacteria was inactivated using formalin fixation in 4% formaldehyde for 4 hr at 37° C. After 3 washes of bacteria with PBS (15 min wash, centrifugation for 20 min at 4000 rpm) the antigen concentration was measured using BCA assay and the antigen was used at 1 mg/mL for immunization. In order to generate Gram-positive bacteria-specific IgG, several bacterial species were used for inoculation: *Staphylococcus aureus, Staphylococcus epidermidis, Enterococcus faecium* and *Enterococcus fecalis*.

The immune serum was purified using affinity chromatography on a protein G sepharose column (GE Healthcare), and reactivity was determined using ELISA. Antibodies cross-reacting with Gram-negative bacteria and fungi were removed by absorption of purified IgG with formalin-fixed Gram-negative bacteria and fungi. The formalin-fixed organisms were prepared similar to as described above and mixed with IgG. After incubation for 2 hrs at room temperature, the preparation was centrifuged to remove bacteria. Final antibody preparation was clarified by centrifugation and used for the preparation of antigen-specific magnetic particles.

Pan-Gram-negative IgG were generated in a similar fashion using inactivated *Enterobacter cloacae, Pseudomonas aeruginosa, Serratia marcescens* and other gram-negative bacteria as immunogens. The IgG fraction of serum was purified using protein-G affinity chromatography as described above.

Similarly, target specific antibodies were generated by inoculation of goats using formalin-fixed bacteria, immunization was performed with 2 or more closely related organisms.

Example 3: Preparation of Antigen-Specific Magnetic Particles

Superparamagnetic particles were synthesized by encapsulating iron oxide nanoparticles (5-15 nm diameter) in a latex core and labeling with goat IgG. Ferrofluid containing nanoparticles in organic solvent was precipitated with ethanol, nanoparticles were resuspended in aqueous solution of styrene and surfactant Hitenol BC-10, and emulsified using sonication. The mixture was allowed to equilibrate overnight with stirring and filtered through 1.2 and 0.45 µm filters to achieve uniform micelle size. Styrene, acrylic acid and divynilbenzene were added in carbonate buffer at pH 9.6. The polymerization was initiated in a mixture at 70° C. with the addition of $K_2S_2O_8$ and the reaction was allowed to complete overnight. The synthesized particles were washed 3 times with 0.1% SDS using magnetic capture, filtered through 1.2, 0.8, and 0.45 µm filters and used for antibody conjugation.

The production of particles resulted in a distribution of sizes that may be characterized by an average size and a standard deviation. In the case of labeling and extracting of bacteria from blood, the average size for optimal performance was found to be between 100 and 350 nm, for example between 200 nm to 250 nm.

The purified IgG were conjugated to prepared particles using standard EDC/sulfo-NHS chemistry. After conjugation, the particles were resuspended in 0.1% BSA which is used to block non-specific binding sites on the particle and to increase the stability of particle preparation.

Example 4: Labeling of Rare Cells Using Excess of Magnetic Nanoparticles

Bacteria, present in blood during blood-stream infection, were magnetically labeled using the superparamagnetic particles prepared in Example 3 above. The spiked samples as described in Example 1 were diluted 3-fold with a Tris-based binding buffer and target-specific particles, followed by incubation on a shaking platform at 37° C. for up to 2 hr. The optimal concentration of particles was determined by titration and was found to be in the range between $1 \times 10^8$ and $5 \times 10^{10}$ particle/mL. After incubation, the labeled targets were magnetically separated followed by a wash step designed to remove blood products. See example 5 below.

Example 5: Magnetic Capture of Bound Bacteria

Blood including the magnetically labeled target bacteria and excess free particles were injected into a flow-through capture cell with a number of strong rare earth bar magnets placed perpendicular to the flow of the sample. With using a flow chamber with flow path cross-section 0.5 mm×20 mm (h×w) and 7 bar NdFeB magnets, a flow rate as high as 5 mL/min was achieved. After flowing the mixture through the channel in the presence of the magnet, a wash solution including heparin was flowed through the channel. The bound targets were washed with heparin-containing buffer one time to remove blood components and to reduce formation of magnetic particle aggregates. In order to effectively wash bound targets, the magnet was removed and captured magnetic material was resuspended in wash buffer, followed by re-application of the magnetic field and capture of the magnetic material in the same flow-through capture cell.

Removal of the captured labeled targets was possible after moving magnets away from the capture chamber and eluting with flow of buffer solution.

What is claimed is:

1. A method for isolating at least one pathogen from a heterogeneous sample, the method comprising:
    obtaining a heterogeneous sample comprising at least one pathogen;
    incubating the sample with a composition comprising a plurality of sets of magnetic particles specific to one or more pathogens, wherein members of a first set of magnetic particles are conjugated to a first class of capture moiety, and members of a second set of magnetic particles are conjugated to a second class of capture moiety;
    separating particle bound pathogen from other components in the sample,
    wherein the first and second classes of capture moiety are different.

2. The method of claim 1, wherein each set of magnetic particles is present at a concentration designed for detection of a specific pathogen in said sample.

3. The method of claim 2, wherein the first and second set of magnetic particles are provided at different concentrations.

4. The method of claim 1, wherein the pathogen is selected from the group consisting of fungi, bacteria and a combination thereof.

5. The method of claim 4, wherein the fungi comprises two or more species of fungi selected from the group consisting of the *Candida* genus, *Aspergillus* genus, and *Cryptococcus* genus.

6. The method of claim 4, wherein the bacteria comprise one or species of bacteria selected from the group consisting of *Staphylococcus* genus, Enterobacteriaceae genus, *Acinetobacter* genus, *Strenotrophomonas* genus, *Pseudomonas* genus, *Neisseria* genus, *Clostridium* genus, and *Enterococcus* genus.

7. The method of claim 1, further comprising lysing the separated pathogen to release nucleic acid.

8. The method of claim 7, further comprising conducting an assay on the nucleic acid to identify the pathogen.

9. The method of claim 8, wherein the assay is selected from the group consisting of a sequencing reaction and a polymerase chain reaction.

10. The method of claim 8, wherein the assay is a multiplex assay.

* * * * *